US 6,957,758 B2
United States Patent — Aranyi
(45) Date of Patent: Oct. 25, 2005

(54) TILT TOP ANVIL FOR A SURGICAL FASTENER DEVICE

(75) Inventor: Ernie Aranyi, Easton, CT (US)

(73) Assignee: TYCO Healthcare Group, LP, Norwalk, CT (US)

( * ) Notice: Subject to any disclaimer, the term of this patent is extended or adjusted under 35 U.S.C. 154(b) by 0 days.

(21) Appl. No.: 10/491,253

(22) PCT Filed: Oct. 4, 2002

(86) PCT No.: PCT/US02/32033

§ 371 (c)(1),
(2), (4) Date: Mar. 30, 2004

(87) PCT Pub. No.: WO03/030745

PCT Pub. Date: Apr. 17, 2003

(65) Prior Publication Data

US 2004/0195289 A1 Oct. 7, 2004

Related U.S. Application Data

(60) Provisional application No. 60/327,727, filed on Oct. 5, 2001.

(51) Int. Cl.$^7$ .............................................. A61B 17/068
(52) U.S. Cl. .................... 227/176.1; 227/19; 227/180.1
(58) Field of Search ............................... 227/19, 176.1, 227/175.1, 180.1, 178.1

(56) References Cited

U.S. PATENT DOCUMENTS

| | | | |
|---|---|---|---|
| 3,388,847 A | 6/1968 | Kasulin et al. | |
| 3,552,626 A | 1/1971 | Astafiev | |
| 3,638,652 A | 2/1972 | Kelley | |
| 4,198,982 A | 4/1980 | Fortner et al. | |
| 4,207,898 A | 6/1980 | Becht | |
| 4,289,133 A | 9/1981 | Rothfuss | |

(Continued)

FOREIGN PATENT DOCUMENTS

| | | |
|---|---|---|
| CA | 908529 | 8/1972 |
| CA | 1136020 | 1/1982 |
| DE | 1057729 | 5/1959 |
| DE | 1835500 | 4/1961 |
| DE | 3301713 | 11/1989 |
| EP | 0152382 | 8/1985 |
| EP | 0173451 | 3/1986 |
| EP | 0190022 | 8/1986 |
| EP | 282157 | 9/1988 |
| EP | 0503689 | 9/1992 |
| FR | 1461464 | 12/1966 |
| FR | 1588250 | 4/1970 |
| FR | 1136020 | 12/1979 |
| FR | 2443239 | 12/1979 |
| GB | 1185292 | 3/1970 |
| GB | 2016991 | 9/1979 |
| GB | 2070499 | 9/1981 |
| NL | 7711347 | 10/1977 |
| WO | 8706448 | 11/1987 |
| WO | 8900406 | 1/1989 |
| WO | 9006085 | 6/1990 |

Primary Examiner—Scott A. Smith

(57) ABSTRACT

A tilt top anvil assembly is provided for use with a surgical stapling device for performing end-to-end anastomosis of tissue. The tilt top anvil assembly included an anvil head, a center rod and a biasing member. The anvil head is pivotally secured to the center rod about a transverse axis which is offset from the longitudinal axis of the center rod. The biasing member is supported on the anvil assembly at a position to urge the anvil head to a tilted reduced profile position. The anvil assembly includes a first abutment surface which is operatively connected to the anvil head is movable into engagement with a second abutment surface formed on a surgical stapling device during approximation of the anvil assembly to move the anvil head from the tilted reduced profile position to an operative firing position. When the anvil assembly is moved to the unapproximated or spaced position, the biasing member is positioned to return the anvil assembly back to its tilted reduced profile position.

24 Claims, 13 Drawing Sheets

U.S. PATENT DOCUMENTS

| | | |
|---|---|---|
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,646,745 A | 3/1987 | Noiles |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,754,909 A | 7/1988 | Barker et al. |
| 4,817,847 A | 4/1989 | Redtenbacher et al. |
| 4,873,977 A | 10/1989 | Avant et al. |
| 4,893,622 A | 1/1990 | Green et al. |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Bianco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,445,644 A | 8/1995 | Pietrafitta et al. |
| 5,447,514 A | 9/1995 | Gerry et al. |
| 5,454,825 A | 10/1995 | Van Leeuwen et al. |
| 5,470,006 A | 11/1995 | Rodak |
| 5,474,223 A | 12/1995 | Viola et al. |
| 5,497,934 A | 3/1996 | Brady et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,632,433 A | 5/1997 | Grant et al. |
| 5,639,008 A | 6/1997 | Gallagher et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,758,814 A | 6/1998 | Gallagher et al. |
| 5,799,857 A | 9/1998 | Robertson et al. |
| 5,826,776 A * | 10/1998 | Schulze et al. .......... 227/176.1 |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balázs et al. |
| 6,264,086 B1 | 7/2001 | McGuckin, Jr. |
| 6,269,997 B1 | 8/2001 | Balázs et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |

| | | |
|---|---|---|
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,595,887 B2 | 7/2003 | Thoma |
| 6,601,749 B2 | 8/2003 | Sullivan et al. |
| 6,605,078 B2 | 8/2003 | Adams |
| 6,616,686 B2 * | 9/2003 | Coleman et al. ............ 606/219 |
| 6,623,227 B2 | 9/2003 | Scott et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,716,222 B2 | 4/2004 | McAlister et al. |
| 6,716,233 B1 | 4/2004 | Whitman |
| 6,742,692 B2 | 6/2004 | Hartwick |
| 6,763,993 B2 | 7/2004 | Bolduc et al. |
| 6,769,590 B2 | 8/2004 | Vresh et al. |

\* cited by examiner

TILT TOP ANVIL FOR A SURGICAL FASTENER DEVICE

This application claims priority from PCT application Ser. No. PCT/US02/32033 filed Oct. 4, 2002 which claims the benefit of U.S. Provisional Application Ser. No. 60/327,727 filed Oct. 5, 2001.

BACKGROUND

1. Technical Field

The present disclosure relates to an anvil assembly for use with a surgical stapling device. More particularly, the present disclosure relates to an anvil assembly having a normally tilted anvil head which is usable with an open or a minimally invasive surgical stapling instrument for performing circular anastomosis of hollow tissue organs.

2. Background of Related Art

Anastomosis is the surgical joining of separate hollow organ sections to allow the sections intercommunicate with each other. Typically, an anastomosis procedure follows surgery in which a diseased or defective section of hollow tissue is removed and the remaining end sections are to be joined. Depending on the desired anastomosis procedure, the end sections may be joined by either circular, end-to-end, end-to-side or side-to-side organ reconstruction methods.

In a circular anastomosis procedure, the two ends of the organ sections are joined by means of a stapling instrument which drives a circular array of staples through the organ end sections and simultaneously cores and removes any overlapping tissue to free a tubular passage. In some applications of a circular anastomosis procedure, on anvil rod having an attached anvil head is mounted to the distal end of a surgical stapling instrument shaft prior to insertion of the instrument into the tissue to be anastomosed. However, in other applications, it is preferable to utilize a detachable anvil rod which may be mounted to the instrument subsequent to positioning of the instrument and the anvil assembly within respective tissue sections. In such instances, the stapling instrument and the anvil assembly are separately delivered to the operative site. Each tissue section is then secured to a respective anvil or staple holding component by a purse string suture. The anvil assembly is mounted to the surgical instrument by inserting a mounting portion of the anvil rod within the distal end of the instrument so that a mounting mechanism within the instrument securely engages the rod. Preparation of the tissue sections to be joined and mounting of the anvil rod to the instrument are performed, preferably, using minimally invasive surgical techniques, i.e., under laparoscopic guidance.

A particular difficulty concerning the aforedescribed approach to perform anastomosis of hollow body organs with a detachable anvil assembly, whether the anastomosis is performed laparoscopically or by other conventional open surgical techniques, concerns delivery and placement of the anvil assembly at the desired location within the hollow organ. This difficulty is attributed to, inter alia, the fact that the anvil assembly, particularly, the rigid, immovable anvil head, presents an obtrusive profile which engages the inner wall of the hollow organ during advancement therethrough. In some instances, the dimension of the anvil head is greater than the cross-sectional dimension of the hollow organ through which it must pass. Consequently, advancement of the anvil assembly through the hollow organ can be traumatic and is impeded and possibly prevented. Furthermore, if a surgical procedure is being performed laparoscopically, difficulty with maneuvering the anvil assembly through the hollow organ may require abandonment of such laparoscopic approach and necessitate conversion to a conventional open laparotomy to complete the anastomosis.

In order to reduce the transverse profile of the anvil assembly during placement and removal of the anvil assembly from a hollow organ, anvil assemblies having a tiltable anvil head have been developed. One such anvil assembly is described in U.S. Pat. No. 6,053,390, filed on May 10, 1999, which is incorporated herein by reference in its entirety. The pivotable anvil head is normally locked in the operative firing position. Upon firing the stapling device, the lock is released and the anvil head is forced to the tilted position by a spring.

Despite recent improvements to circular anastomosis instruments, a need still exists for an improved anvil assembly usable with a circular anastomosis instrument which includes an anvil head that is easier to deliver into hollow tissues to be joined, that can be delivered with less contact with such tissues, and also that automatically pivots between tilted and operative positions during delivery and removal of the instrument from the tissues.

SUMMARY

In accordance with the present disclosure, a tilt top anvil assembly is provided for use with a surgical stapling device for performing end-to-end anastomosis of tissue. The tilt top anvil assembly includes an anvil head, a center rod and a biasing member. The anvil head is pivotally secured to the center rod about a transverse axis which is offset from the longitudinal axis of the center rod. The biasing member is supported on the anvil assembly at a position to urge the anvil head to a tilted reduced profile position. The anvil assembly includes a first abutment surface which is operatively connected to the anvil head and is movable into engagement with a second abutment surface formed on a surgical stapling device during approximation of the anvil assembly to move the anvil head from the tilted reduced profile position to an operative firing position.

In one preferred embodiment, the center rod includes a longitudinal bore. An outer sleeve is slidably positioned within the longitudinal bore and an inner sleeve is slidably positioned within the outer sleeve. The inner and outer sleeves are pivotally connected to the anvil head by respective links. The biasing member is positioned within the longitudinal bore to urge the inner sleeve towards the anvil head to urge the anvil head to the tilted reduced profile position. The outer sleeve includes a first abutment member which is positioned to engage a second abutment surface supported on a surgical stapling device when the anvil assembly is moved from a position spaced from a shell assembly of the surgical stapling device to an approximated position in close alignment with the shell assembly of the surgical stapling device. Upon engagement between the first and second abutment surfaces and continued approximation, the anvil head is pivoted from the tilted reduced profile position to the operative firing position. When the anvil assembly is moved back to the spaced position, the biasing member urges the anvil head back to the tilted reduced profile position. Thus, the anvil head is automatically moved to a tilted reduced profile position during delivery and removal of the instrument from the anastomatic site. Alternatively, other linkage mechanisms for pivoting the anvil head from the tilted reduced profile position to the operative firing position are envisioned.

In another preferred embodiment, a shell assembly of the surgical stapling device may include an annular sleeve positioned therein. Preferably, the second abutment surface is formed on the annular sleeve at a position to engage the first abutment surface on the anvil assembly. Alternately, the second abutment may be positioned at other locations on the surgical stapling device.

BRIEF DESCRIPTION OF THE DRAWINGS

Preferred embodiments of the presently disclosed tilt top anvil assembly are described hereinbelow with reference to the drawings wherein.

DETAILED DESCRIPTION OF PREFERRED EMBODIMENTS

Figure 1:
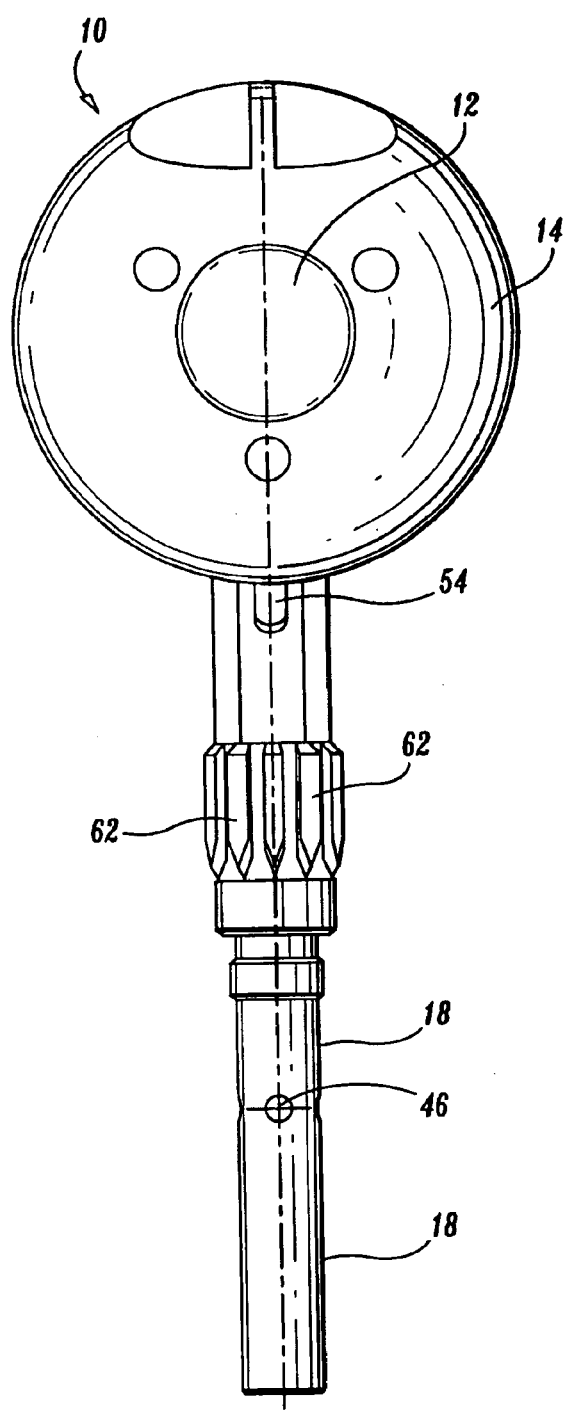
FIG. 1 is a side view of one preferred embodiment of the presently disclosed tilt top anvil assembly with the anvil head in the tiled reduced profile position.

Preferred embodiments of the presently disclosed tilt top anvil assembly will now be described in detail with reference to the drawings in which like reference numerals designate identical or corresponding elements in each of the several views.

Figure 2:
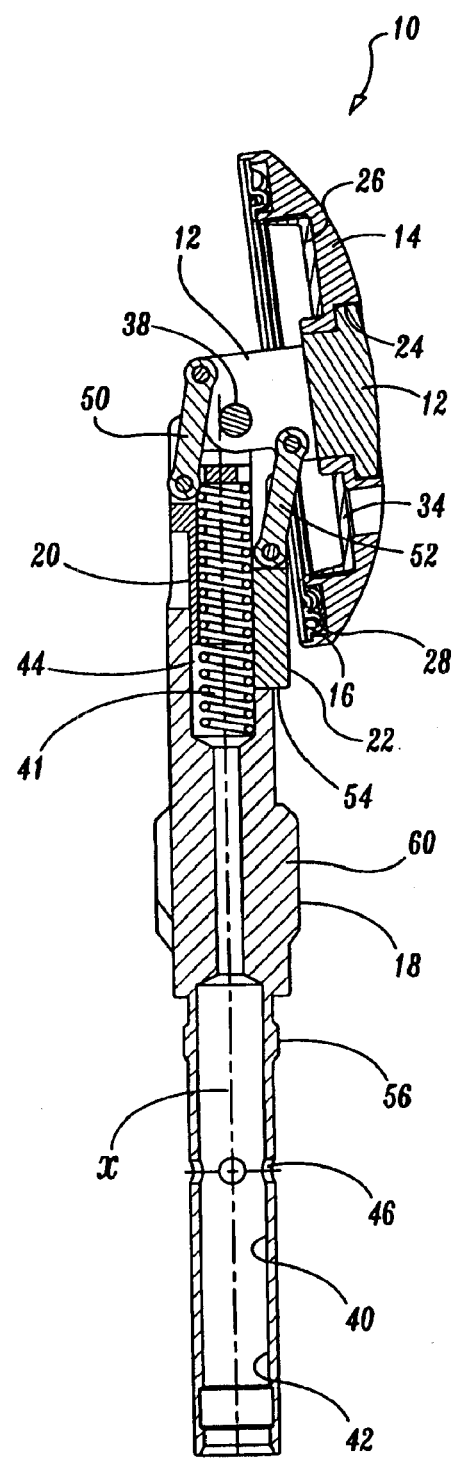
FIG. 2 is a side cross-sectional view of the tilt top anvil assembly shown in FIG. 1 with the anvil head in the tilted reduced profile position.
Figure 1A:
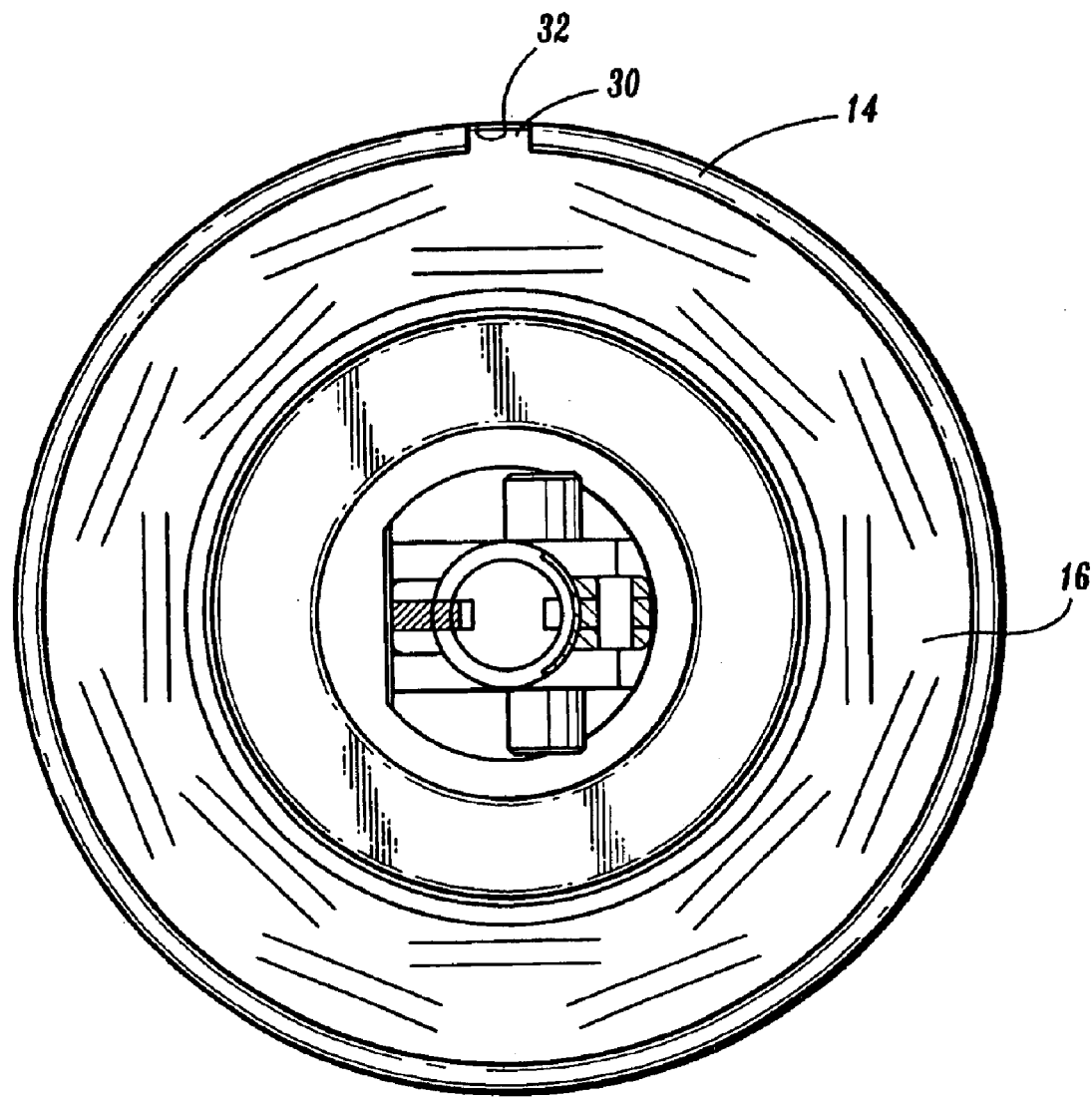
FIG. 1A is a bottom partial cross-sectional view of the anvil assembly shown in FIG. 1.
Figure 3:
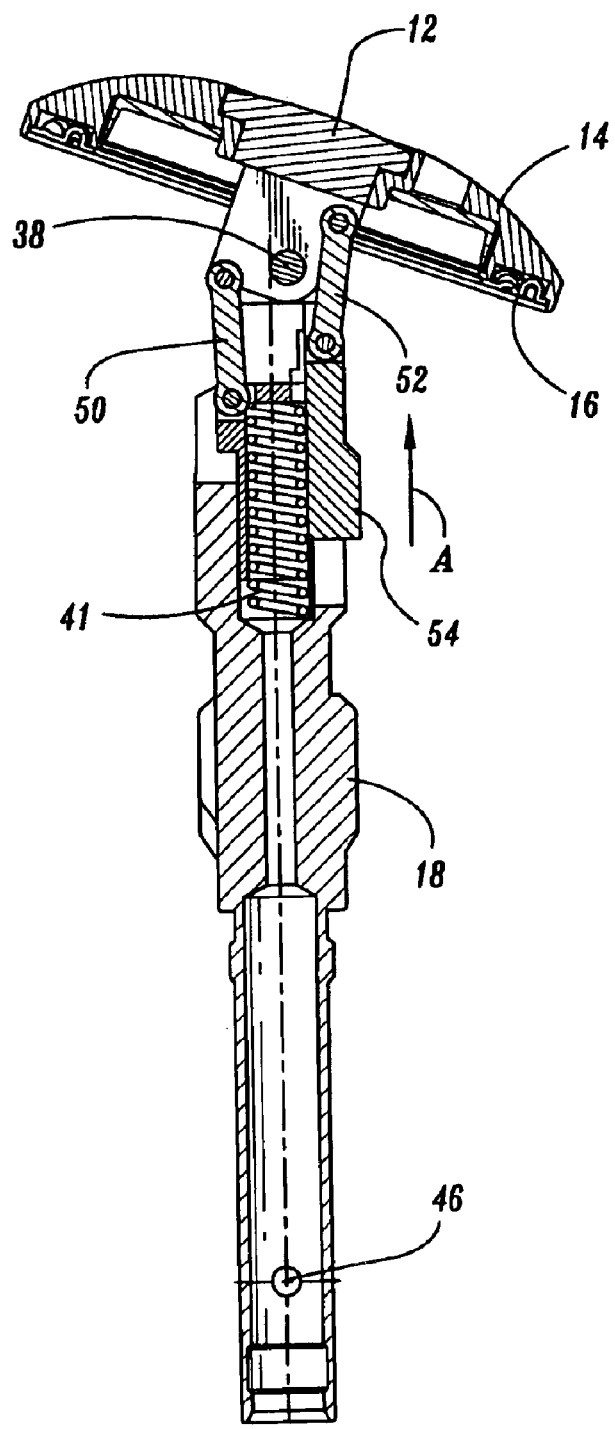
FIG. 3 is a side cross-sectional view of the tilt top anvil assembly shown in FIG. 1 with the anvil head positioned between the tilted reduced profile position and the operative firing position.

Referring to FIGS. 1 and 2, anvil assembly 10 includes an anvil post 12, an anvil head 14, an anvil plate 16, a center rod 18, an inner sleeve 20 and an outer sleeve 22. Anvil head 14 includes a centrally located through bore 24 dimensioned to receive anvil post 1,2, an inner annular recess 26 and an outer annular recess 28. Outer annular recess 28 is configured to receive anvil plate 16. Anvil plate 16 includes a tab 30 (FIG. 1A) which is dimensioned to be received within a slot 32 formed in anvil head 14. Tab 30 and slot 32 cooperate to position anvil plate 16 in the proper orientation within outer recess 28. Inner annular recess 26 is configured to receive a cutting ring 34 that includes a central opening dimensioned to be positioned about anvil post 12 and a portion of anvil head 14 defining annular recess 26.

Figure 4:
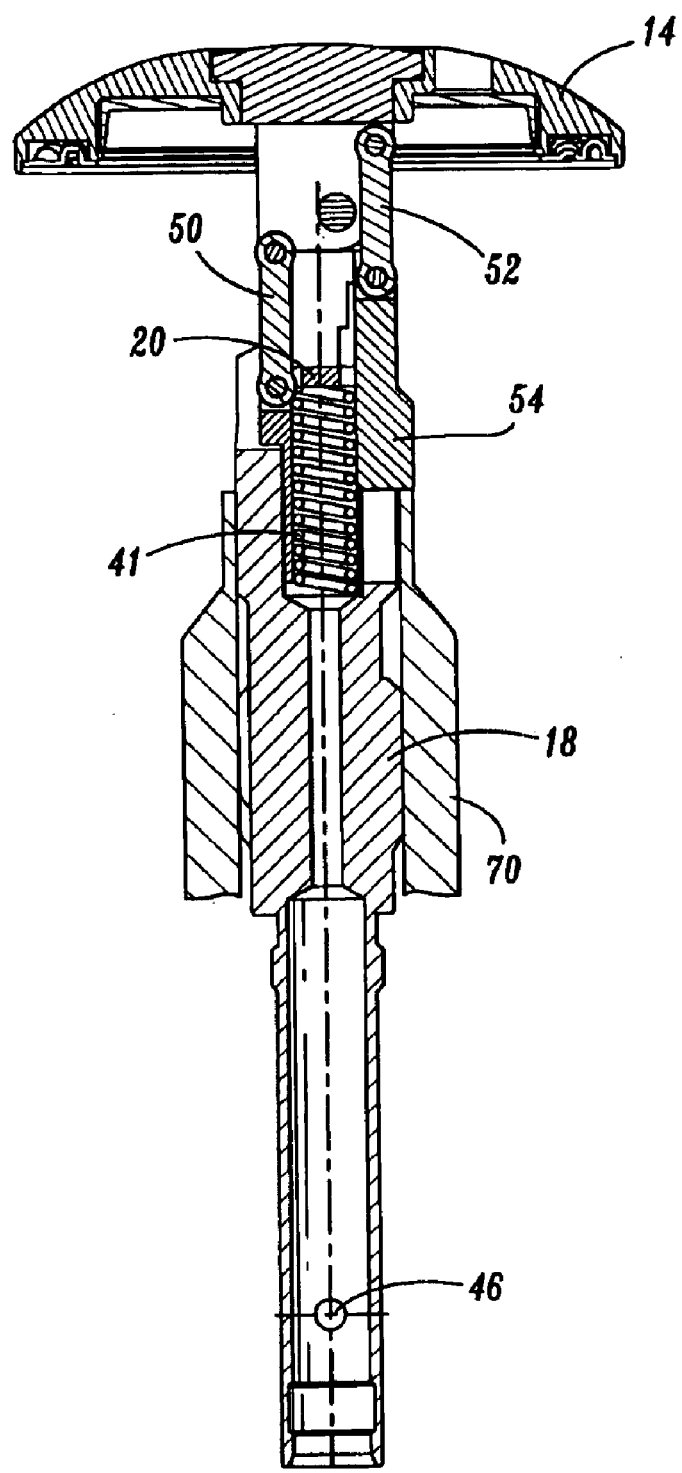
FIG. 4 is a side cross-sectional view of the tilt top anvil assembly shown in FIG. 1 with the anvil head in the operative firing position.

Anvil post 12 includes a transverse bore for receiving a pivot member 38. Pivot member 38 pivotally connects anvil post 12 to one end of center rod 18. Preferably, pivot member 38 includes a pin or post which defines a transverse axis which is spaced laterally from the longitudinal "x" axis of center rod 18 such that anvil head 14 can pivot approximately 90 degrees from an operative position (FIG. 4) in which a plane defined by the tissue contact surface of the anvil head 14 is substantially perpendicular to the longitudinal axis of center rod 18 to a tilted reduced profile position (FIG. 2) in which anvil head 14 is substantially parallel to the longitudinal axis of center rod 18. Alternately, other types of pivot members at a variety of locations in relation to the axis "x" of the center rod may be incorporated into the anvil assembly.

Center rod 18 includes a throughbore 40 having a first end 42 and a second end 44. Preferably first end 42 includes at least one bore 46 dimensioned to receive a suture or the like to facilitate positioning of anvil assembly 10 within a hollow organ. Second end 44 of throughbore 40 is dimensioned to slidably receive inner sleeve 20 and outer sleeve 22. Outer sleeve 22 is slidably positioned within second end 44 of throughbore 40, and a portion of inner sleeve 20 is slidably positioned within outer sleeve 22. A spring or biasing member, e.g., coil spring 41, is positioned in second end 44 of throughbore 40 abutting inner sleeve 20 to urge inner sleeve 20 to an advanced position toward the distal end of anvil assembly 10. A drive link 52 is pivotally connected at one end to outer sleeve 22 and at the other end to anvil post 12. A return link 50 is pivotally connected at one end to inner sleeve 20 and at the other end to anvil post 12. Outer sleeve 22 includes an abutment 54 (FIG. 4) which will be discussed in further detail below.

Center rod 18 is dimensioned to releasably engage an anvil retainer (not shown) of a circular anastomosis surgical stapling device. One such surgical stapling device having an anvil retainer and with which anvil assembly 10 may be used is disclosed in U.S. provisional patent application Ser. No. 60/281,259, filed Apr. 3, 2001, ("the '259 application") which is incorporated herein in its entirety by reference. Center rod 18 includes an annular projection 56 which is dimensioned to lockingly engage the anvil retainer. A guide collar 60 is monolithically formed with center rod 18. Alternately, guide collar 60 may include a sleeve which is separately formed from center rod 18. Guide collar 60 includes circumferentially spaced splines 62 which function to align anvil assembly 10 with the shell assembly 100 (FIGS. 5–8) of the surgical stapling device during movement of the anvil assembly from a positioned spaced from a shell assembly of the surgical stapling device to an approximated position in close alignment with the shell assembly.

Inner sleeve 20 is moveable between an advanced position and a retracted position. The inner sleeve biasing member 41 normally urges inner sleeve 20 to the advanced position. In the advanced position, return link 50 is moved towards anvil head 14 to pivot anvil head 14 about pivot member 38 to the tilted reduced profile position (FIG. 2).

Figure 5:
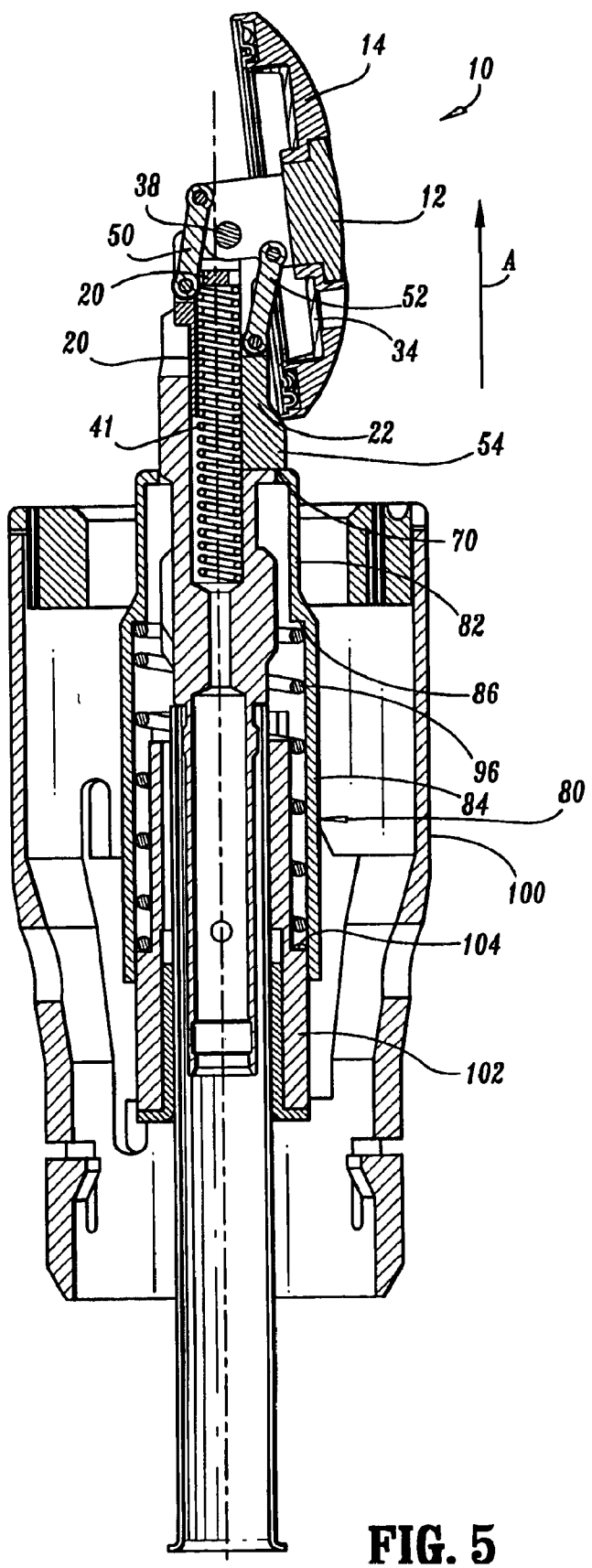
FIG. 5 is a side cross-sectional view of the tilt top anvil assembly shown in FIG. 1 with the anvil head positioned in the tilted reduced profile position and secured to the shell assembly of a surgical stapling device.
Figure 6:
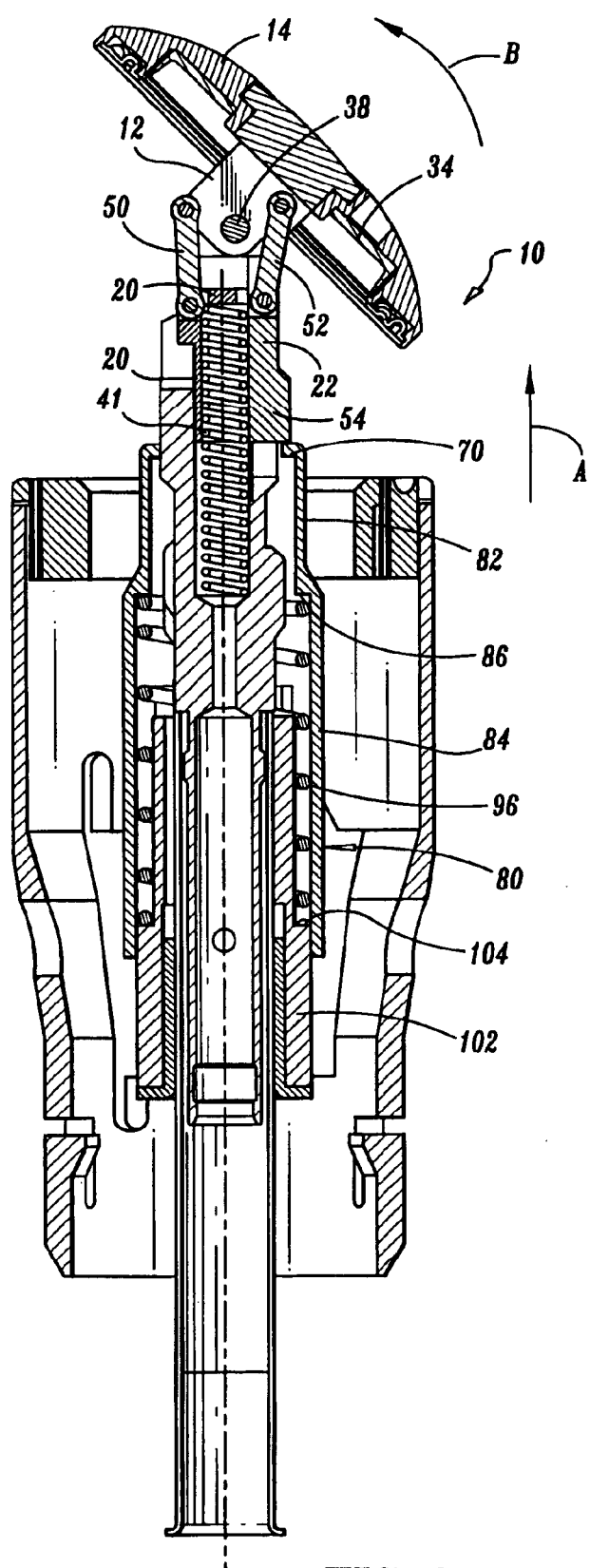
FIG. 6 is a side cross-sectional view of the tilt top anvil assembly shown in FIG. 1 with the anvil head positioned between the tilted reduced profile position and the operative firing position.
Figure 7:
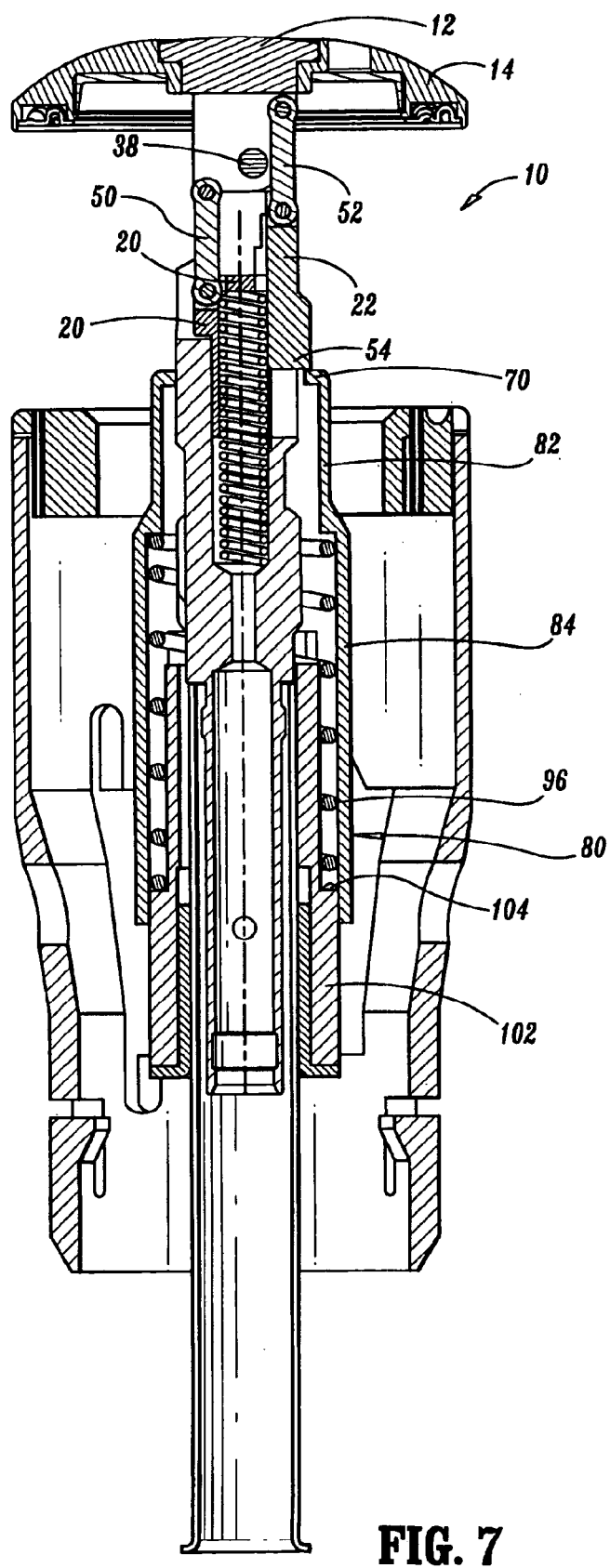
FIG. 7 is a side cross-sectional view of the tilt top anvil assembly shown in FIG. 1 with the anvil head positioned in the operative firing position.
Figure 8:
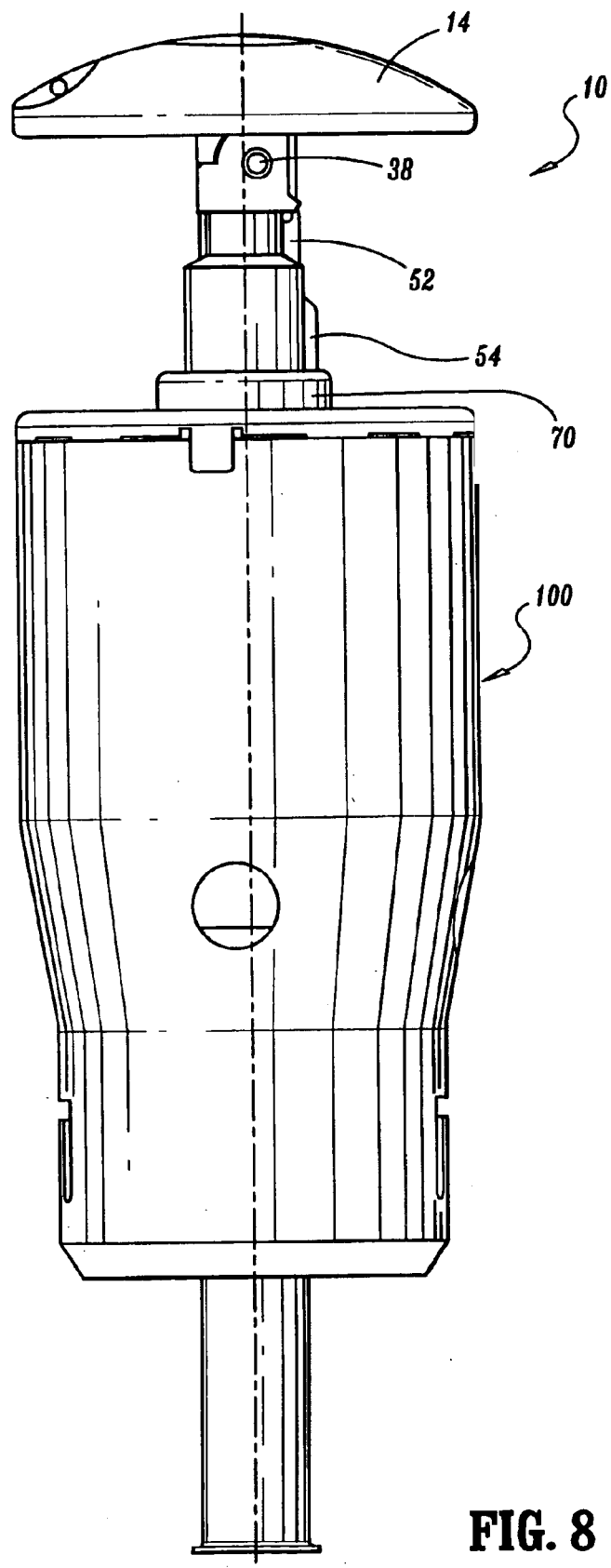
FIG. 8 is a side view of the tilt top anvil assembly shown in FIG. 1 with the anvil head positioned in the operative firing position and secured to the shell assembly of a surgical stapling device.
Figure 9:
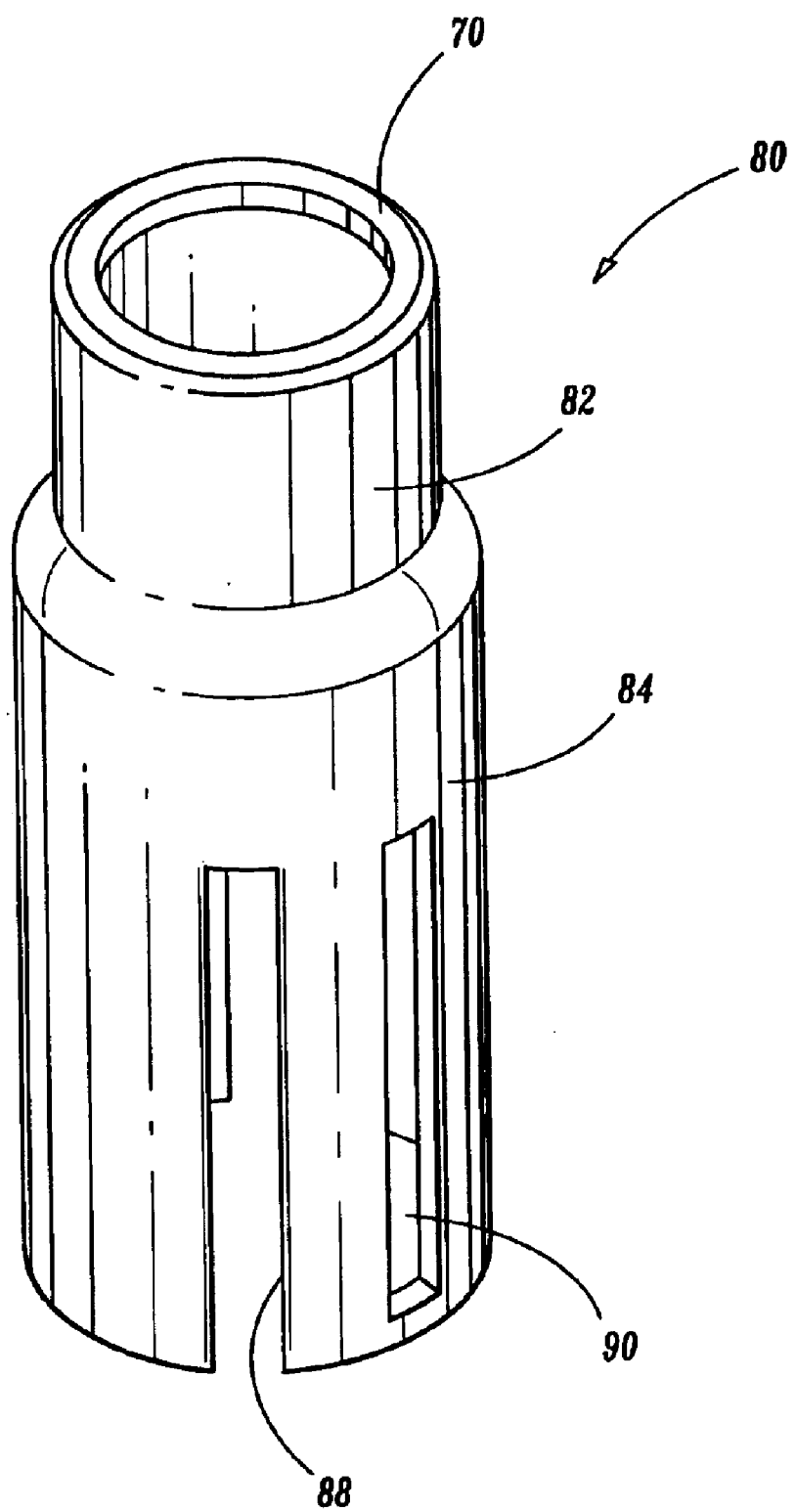
FIG. 9 is a top perspective view of the annular sleeve of the shell assembly of a surgical stapling device with which the presently disclosed tilt top anvil may be used.
Figure 10:
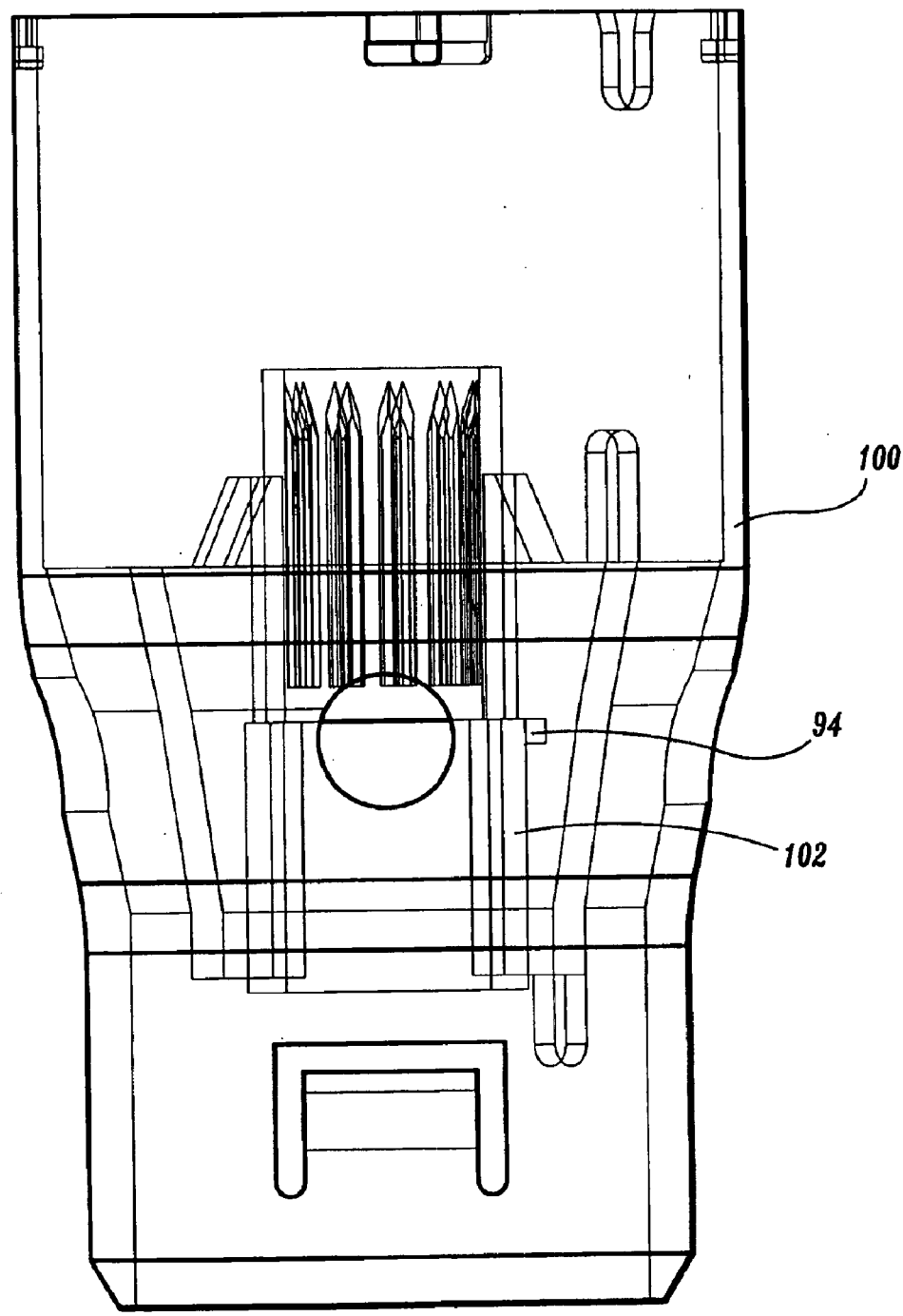
FIG. 10 is a side cross-sectional view of the body of the shell assembly shown in FIG. 8.
Figure 11:
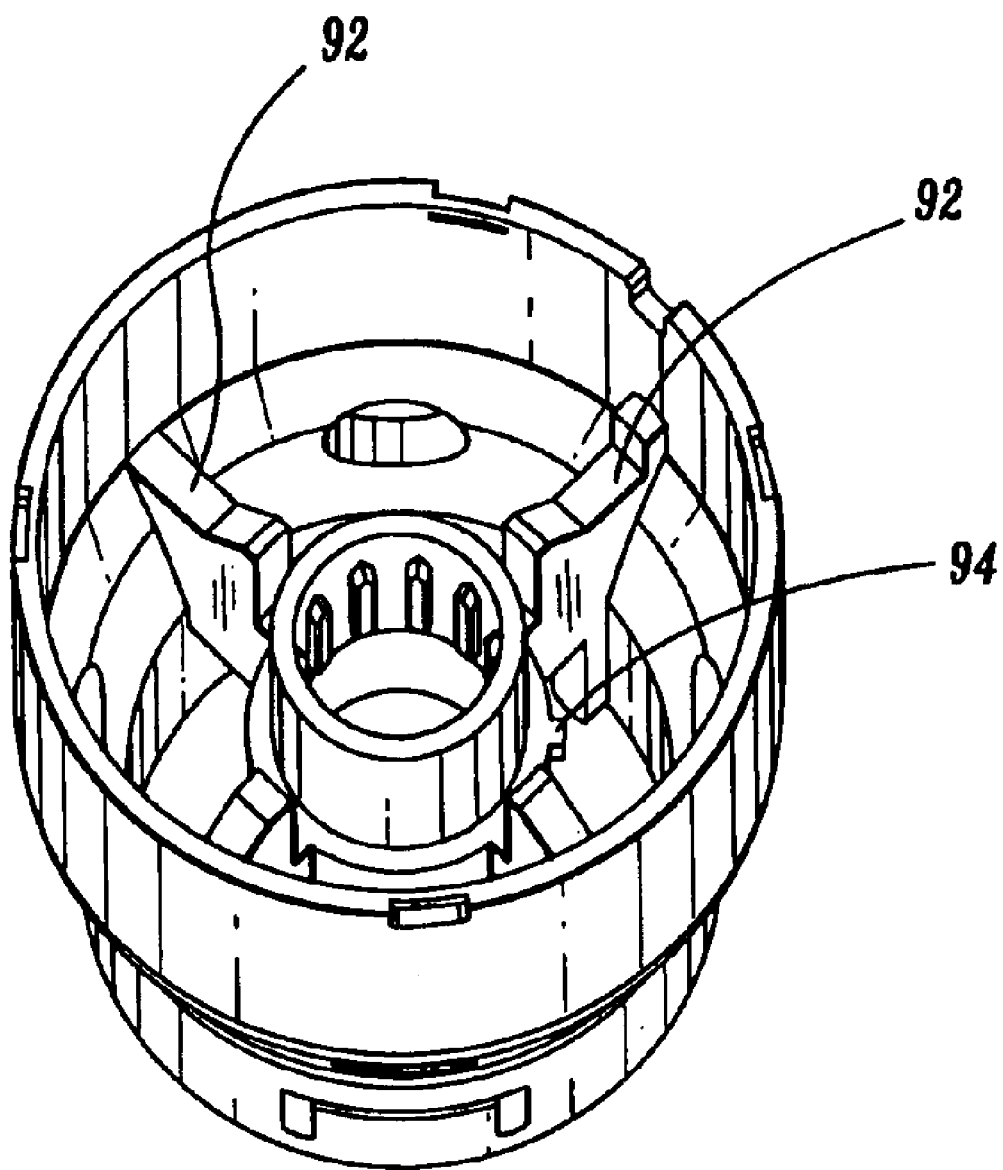
FIG. 11 is a top view of the body of the shell assembly shown in FIG. 10.
Figure 12:
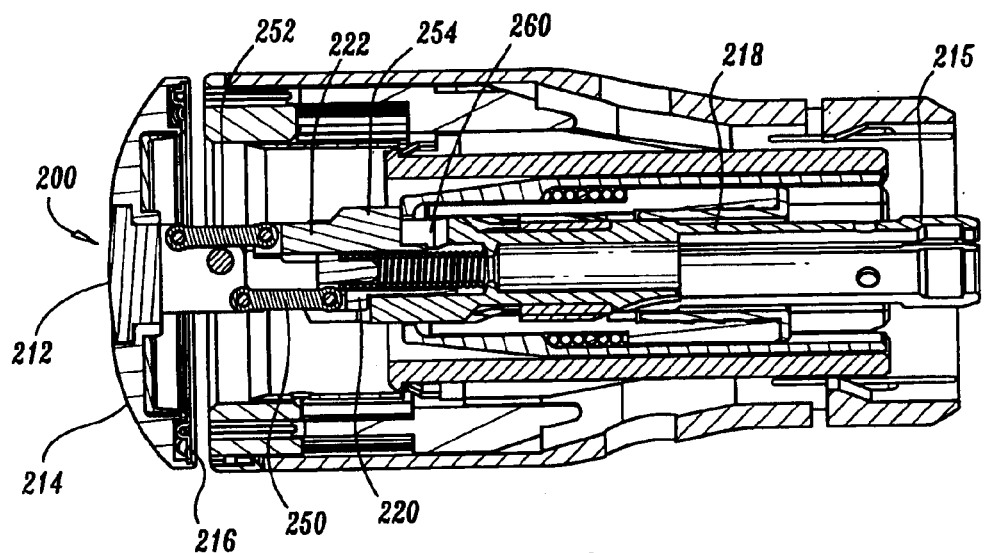
FIG. 12 is a side cross-sectional view of another preferred embodiment of the presently disclosed tilt top anvil assembly secured to the shell assembly of a surgical stapling device with the anvil head positioned in the operative firing position.

Referring to FIGS. 5–8, anvil assembly 10 is moved to the operative position by advancing abutment 54 of outer sleeve 22 towards anvil head 14. This will occur automatically when anvil assembly 10 is secured to the anvil retainer of a surgical stapling device and the device is approximated. More specifically, during approximation of a surgical stapling device, abutment 54 is engaged by an abutment 70 positioned on or within the shell assembly 100 of a surgical stapling device to advance outer sleeve 22 in the direction indicated by arrow "A" in FIGS. 5 and 6 towards anvil head 14. Abutment 70 may be provided on an annular sleeve 80 adapted to be fitted within the shell assembly of a surgical stapling device. Movement of outer sleeve 22 towards anvil head 14 advances drive link 52 towards anvil head 14 against the bias of the inner sleeve biasing member 41 to pivot anvil head 14 in the direction indicated by arrow "B" in FIG. 6 from the tilted reduced profile position (FIG. 5) to the operative firing position (FIG. 7). Thereafter, when the surgical stapling device is moved from the approximated position to the unapproximated or spaced position and abutment 54 is moved distally out of engagement with abutment 70, inner sleeve biasing member 41 will return anvil assembly 10 to its tilted reduced profile position.

Referring to FIGS. 5–11, one preferred embodiment of annular sleeve 80 including abutment 70 is illustrated. Annular sleeve 80 includes a first cylindrical body portion 82 and a second cylindrical body portion 84. Second cylindrical body portion 84 has a diameter larger than that of the first cylindrical body portion 82 such that a shoulder 86 is defined on an internal wall of sleeve 80 between first and second portions 82 and 84. Second body portion 84 includes four elongated cutouts 88 (FIG. 9, only one is shown) and a window 90. Cutouts 88 are dimensioned to be slidably positioned over ribs 92 (FIG. 11) formed within shell assembly 100. Sleeve 80 is formed of a material having some flexibility to facilitate positioning of window 90 over a stop 94 (FIG. 10) formed within shell assembly 100, such that stop 94 is axially slidably confined within window 90. Alternately, sleeve 80 may be configured differently, i.e., sleeve 80 need not be annular but rather may include an abutment, fixed or movable, having any configuration positioned to engage the first abutment on the anvil assembly.

In use, second body portion 84 of annular sleeve 80 is positioned within shell assembly 100 with second body portion 84 slidably positioned over inner cylindrical portion 102 of shell assembly 100 (FIGS. 5–7), cutouts 88 positioned over ribs 92 (FIG. 11) and window 90 positioned over stop 94. A spring biasing member, preferably a coil spring 96, is positioned between shoulder 86 of annular sleeve 80 and a cutout 104 formed on inner cylindrical portion 102 of shell assembly 100. Biasing member 96 is positioned to urge annular sleeve 80 towards anvil head 14. Abutment 70 is formed on the distal end of first cylindrical portion 82 of annular sleeve 80.

As discussed above, when anvil assembly 10 is secured to a surgical stapling device and the device is approximated, abutment 54 on outer sleeve 22 will engage abutment 70 (FIGS. 5–7). When this occurs, since biasing member 96 has a greater compressive strength than biasing member 41, outer sleeve 22 will be advanced towards anvil head 14 when the anvil assembly is approximated further to move anvil head 14 from the tilted reduced profile position (FIG. 5) to the operative firing position (FIG. 7). When anvil head 14 has been pivoted to the operative position and outer sleeve 22 cannot be advanced any further towards anvil head 14, further approximation of the anvil head 14 and shell assembly 100 will compress biasing member 96 and cause annular sleeve 80 to retract into shell assembly 100 in a telescoping fashion about inner cylindrical portion 102 of shell assembly 100.

Figure 13:
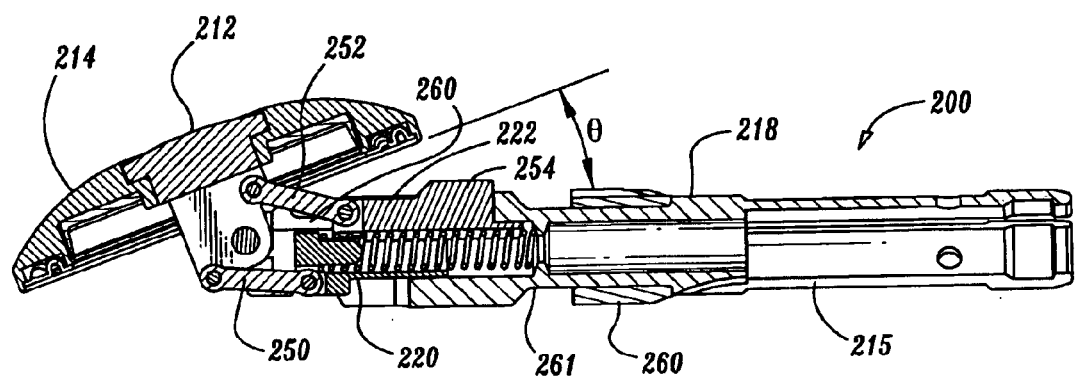
FIG. 13 is a side cross-sectional view of the tilt top anvil assembly shown in FIG. 12 with the anvil head in the tilted reduced profile position.
Figure 14:
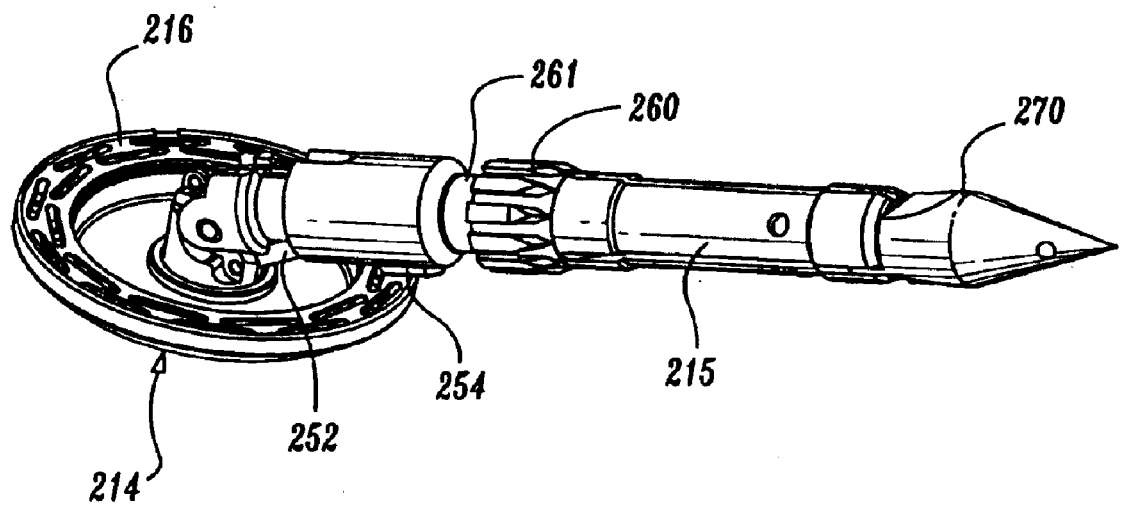
FIG. 14 is a side perspective view of the tilt top anvil assembly shown in FIG. 12 with the anvil head positioned in the tilted reduced profile position and a removable trocar engaged with the center rod.
Figure 15:
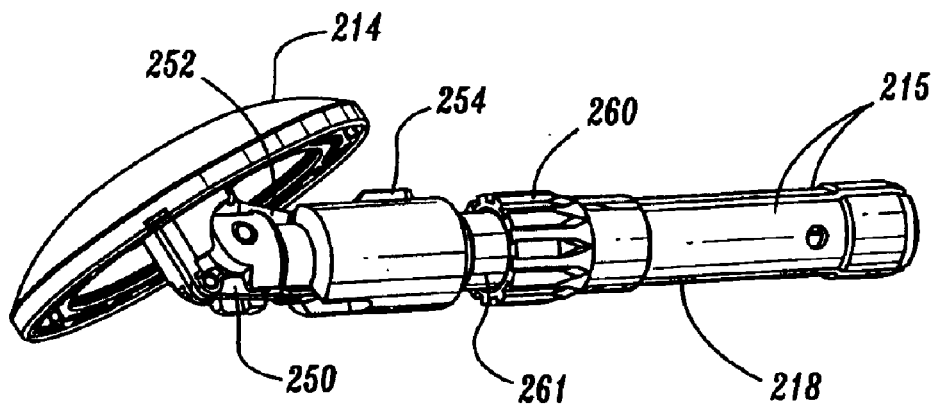
FIG. 15 is a side perspective view from a different side of the tilt top anvil assembly shown in FIG. 14 with the removable trocar removed from the anvil center rod.

FIGS. 12–15 illustrate another preferred embodiment of the presently disclosed tilt top anvil assembly shown generally as tilt top anvil assembly 200. Tilt top anvil assembly 200 is substantially the same as tilt top anvil 10 and includes anvil post 212, anvil head 214, anvil plate 216, center rod 218, inner sleeve 220 and outer sleeve 222. A drive link 252 is pivotally connected at one end to outer sleeve 222 and at the other end to anvil post 212. A return link 250 is pivotally connected at one end to inner sleeve 220 and at the other end to anvil post 212. Outer sleeve 222 includes abutment 254. Center rod 218 includes a plurality of resilient arms 215 which flex outwardly to releasably engage an anvil retainer (not shown) of a surgical stapling device or a removable trocar 270 (FIG. 14).

Tilt top anvil assembly 200 differs from tilt top anvil assembly 10 in a few respects which will be described hereinbelow. As illustrated in FIG. 13, tilt top anvil assembly 200 is configured to permit anvil head 214 to pivot with respect to center rod 218 to define an angle Θ of about 20° with respect to the longitudinal axis of the assembly. (Note: anvil head 14 tilts to a position substantially parallel to the longitudinal axis of tilt top anvil assembly 10). The degree of tilt of anvil head 214 is controlled by varying the length of slot 260 in center rod 218 through which abutment 254 is movably positioned. Angle Θ can be increased by shortening the length of slot 260 and decreased by increasing the length of slot 260. It is preferred that angle Θ is not less than about 20°. When angle Θ is greater than about 20°, there is less tissue resistance to pivoting anvil head 214 to the operative position when the device is approximated. However, it is envisioned that there are surgical applications in which it would be desirable to have an angle Θ of less than 20°.

Center rod 214 includes a cutout 261 positioned adjacent splines 262. Cutout 261 provides an area on center rod 214 which can be easily grasped by a surgeon using a grasping tool.

The above-described anvil assembly is particularly suited for use in minimally invasive gastric bypass procedures. Such a procedure is described in PCT application Ser. No. PCT/US01/07105, filed Mar. 5, 2001, and U.S. Provisional patent application Ser. No. 60/187,121, filed Mar. 6, 2000, both of which are incorporated herein in their entirety by reference. Alternately, the above described anvil assembly may be used in other surgical procedures especially those in which a reduced profile anvil assembly is desirable.

It will be understood that various modifications may be made to the embodiments disclosed herein. For example, abutment 70 need not be formed on a telescoping annular sleeve but rather may be a non-annular abutment which is movably or fixedly supported within the shell assembly of a surgical stapling device. Therefore, the above description should not be construed as limiting, but merely as exemplifications of preferred embodiments. Those skilled in the art will envision other modifications within the scope and spirit of the claims appended hereto.

What is claimed is:

1. A tilt top anvil assembly comprising:
   an anvil head;
   a center rod; and
   an abutment positioned on the anvil assembly;
   wherein the anvil head is pivotally secured to the center rod and is pivotable between an operative firing position and a tilted reduced profile position, and the abutment being movable to move the anvil head between the tilted reduced profile position and the operative firing position.

2. A tilt top anvil assembly according to claim 1, further including a biasing member positioned to urge the anvil head to the tilted reduced profile position.

3. A tilt top anvil assembly according to claim 2, wherein the center rod includes a longitudinal throughbore, the anvil assembly further including an inner sleeve and an outer sleeve, the outer sleeve being slidably positioned within the center rod throughbore and being operably connected to the anvil head and the inner sleeve being slidably positioned within the outer sleeve and being operably connected to the anvil head, wherein the biasing member is positioned to urge the inner and outer sleeves to a position to move the anvil head to the tilted reduced profile position.

4. A tilt top anvil assembly according to claim 3, further including a drive link pivotally connected between the outer sleeve and the anvil head and a return link pivotally connected between the anvil head and the inner sleeve.

5. A tilt top anvil assembly according to claim 4, wherein the abutment is positioned on the outer sleeve, the abutment being positioned to engage a surface on a surgical stapling device during approximation of the anvil assembly to move the anvil assembly from the tilted reduced profile position to the operative firing position.

6. A tilt top anvil assembly according to claim 1, wherein the anvil head is pivotally secured to the center rod by a pivot member, the pivot member having a transverse axis which is offset from the longitudinal axis of the center rod.

7. A tilt top anvil assembly according to claim 1, wherein the center rod includes a guide collar having a plurality of splines.

8. A tilt top anvil assembly according to claim 1, wherein the anvil head includes a cutting ring positioned to engage a knife provided on a surgical stapling device.

9. A tilt top anvil assembly according to claim 1, wherein the center rod includes at least one through bore dimensioned to receive a suture.

10. A tilt top anvil assembly according to claim 1, wherein in the tilted reduced profile position, an angle $\Theta$ defined between the longitudinal axis of the anvil assembly and a plane defined by a tissue contact surface of the anvil head is not less than about 20°.

11. A surgical stapling device comprising:
a handle portion;
an endoscopic body portion extending distally from the handle portion;
a shell assembly supported on the distal end of the endoscopic portion, the shell assembly housing a plurality of surgical fasteners; and
a tilt top anvil assembly configured to be positioned adjacent the shell assembly, the tilt top anvil assembly including an anvil head, and a center rod, the anvil head being pivotally secured to the center rod and being pivotable between an operative firing position and a tilted reduced profile position, the anvil assembly including an abutment positioned to move the anvil head from the tilted reduced profile position to the operative firing position in response to approximation of the anvil assembly and the shell assembly.

12. A surgical stapling device according to claim 11, wherein the anvil assembly includes a biasing member which is positioned to urge the anvil head to the tilted reduced profile position.

13. A surgical stapling device according to claim 12, wherein the center rod includes a longitudinal throughbore, the anvil assembly further including an inner sleeve and an outer sleeve, the outer sleeve being slidably positioned within the center rod throughbore and being operably connected to the anvil head and the inner sleeve being slidably positioned within the outer sleeve and being operably connected to the anvil head, wherein the biasing member is positioned to urge the inner and outer sleeves to a position to move the anvil head to the tilted reduced profile position.

14. A surgical stapling device according to claim 13, further including a drive link pivotally connected between the outer sleeve and the anvil head and a return link pivotally connected between the anvil head and the inner sleeve.

15. A surgical stapling device according to claim 13, wherein the abutment is positioned on the outer sleeve, the abutment being positioned to engage a surface formed on the surgical stapling device during approximation of the anvil assembly to move the anvil assembly from the tilted reduced profile position to the operative firing position.

16. A surgical stapling device according to claim 12, wherein the anvil head is pivotally secured to the center rod by a pivot member, the pivot member having a transverse axis which is offset from the longitudinal axis of the center rod.

17. A surgical stapling device according to claim 12, wherein the center rod includes a guide collar having a plurality of splines.

18. A surgical stapling device according to claim 12, wherein the anvil head includes a cutting ring positioned to engage a knife provided on the surgical stapling device.

19. A surgical stapling device according to claim 12, wherein the center rod includes at least one through bore dimensioned to receive a suture.

20. A surgical stapling device according to claim 12, wherein the abutment member includes a first abutment member supported on the tilt top anvil assembly and a second abutment member supported adjacent the shell assembly, the first abutment member being operably connected to the anvil head and being movable during movement of the anvil assembly from a position spaced from the shell assembly to an approximated position into engagement with the second abutment member to move the anvil head from the tilted reduced profile position to the operative firing position.

21. A surgical stapling device according to claim 20, further including an annular sleeve supported within the shell assembly, the second abutment member being formed on the annular sleeve.

22. A surgical stapling device according to claim 21, wherein the annular sleeve is movable from an extended position to a retracted position, a second biasing member being positioned to urge the annular sleeve to the extended position.

23. A surgical stapling device according to claim 22, wherein the second biasing member has a greater compressive strength than the first biasing member such that during movement of the anvil assembly from the spaced to the approximated position, when the first abutment member engages the second abutment member, the anvil head is moved from the tilted reduced profile position to the operative firing position prior to movement of the annular sleeve from the extended position to the retracted position.

24. A tilt top anvil assembly according to claim 11, wherein in the tilted reduced profile position, an angle $\Theta$ defined between the longitudinal axis of the anvil assembly and a plane defined by a tissue contact surface of the anvil head is not less than about 20°.

* * * * *